United States Patent
Quinn et al.

(10) Patent No.: US 10,398,325 B2
(45) Date of Patent: Sep. 3, 2019

(54) BLOOD PRESSURE CUFF

(71) Applicant: Welch Allyn, Inc., Skaneateles Falls, NY (US)

(72) Inventors: David E. Quinn, Auburn, NY (US); John A. Lane, Weedsport, NY (US); Raymond A. Lia, Auburn, NY (US); Sean R. Karla, Syracuse, NY (US); Robert L. Vivenzio, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 355 days.

(21) Appl. No.: 15/188,119

(22) Filed: Jun. 21, 2016

(65) Prior Publication Data

US 2016/0296128 A1    Oct. 13, 2016

Related U.S. Application Data (60) Continuation of application No. 14/687,335, filed on Apr. 15, 2015, now Pat. No. 9,386,928, which is a division of application No. 13/220,314, filed on Aug. 29, 2011, now Pat. No. 9,028,419.

(51) Int. Cl.
*A61B 5/022* (2006.01)
*A61B 5/00* (2006.01)

(52) U.S. Cl.
CPC ........ *A61B 5/02233* (2013.01); *A61B 5/6831* (2013.01)

(58) Field of Classification Search
None
See application file for complete search history.

(56) References Cited

U.S. PATENT DOCUMENTS

| | | | |
|---|---|---|---|
| 1,043,521 A | 11/1912 | Hoobler | |
| 3,654,931 A * | 4/1972 | Hazlewood | A61B 17/135 606/202 |
| 3,906,937 A | 9/1975 | Aronson | |
| 4,210,154 A | 7/1980 | Klein | |
| 4,572,205 A | 2/1986 | Sjonell | |
| 4,771,790 A | 9/1988 | Yamasawa et al. | |
| 4,860,761 A | 8/1989 | Yamasawa et al. | |
| 4,920,971 A | 5/1990 | Blessinger | |
| 5,069,219 A | 12/1991 | Knoblich | |
| 5,396,894 A * | 3/1995 | Eide | A61B 5/02233 600/499 |
| 5,413,582 A | 5/1995 | Eaton | |
| 5,660,182 A | 8/1997 | Kuroshaki et al. | |

(Continued)

FOREIGN PATENT DOCUMENTS

JP    10-14892    1/1998

OTHER PUBLICATIONS

The Australian Examination Report dated Mar. 2, 2016 for Australian patent application No. 2012300520, a counterpart foreign application of U.S. Pat. No. 9,028,419, 3 pages.

(Continued)

*Primary Examiner* — Michael R Bloch
(74) *Attorney, Agent, or Firm* — Lee & Hayes, P.C.

(57) ABSTRACT

A blood pressure cuff includes a first bladder having a width, and a length transverse to the width. The blood pressure cuff also includes a second bladder connected to the first bladder and a port fluidly connected to at least one of the first and second bladders.

17 Claims, 9 Drawing Sheets

(56) References Cited

U.S. PATENT DOCUMENTS

| | | | |
|---|---|---|---|
| 5,733,304 A | 3/1998 | Spence | |
| 6,336,901 B1 | 1/2002 | Itonaga et al. | |
| 6,527,727 B2 * | 3/2003 | Itonaga | A61B 5/02233 600/490 |
| 6,694,821 B2 | 2/2004 | Yamakoshi et al. | |
| 9,033,891 B2 | 5/2015 | Aranciva | |
| 2002/0002340 A1 | 1/2002 | Nishibayashi | |
| 2002/0170359 A1 | 11/2002 | Yamakoshi et al. | |
| 2004/0098035 A1 * | 5/2004 | Wada | A61B 17/1325 606/201 |
| 2006/0129049 A1 | 6/2006 | Sano et al. | |
| 2006/0135873 A1 * | 6/2006 | Karo | A61B 5/02233 600/499 |
| 2006/0293600 A1 * | 12/2006 | Wawro | A61B 5/02141 600/490 |
| 2007/0073174 A1 | 3/2007 | Aranciva | |
| 2009/0043215 A1 * | 2/2009 | Grassl | A61B 5/02233 600/499 |
| 2010/0106029 A1 | 4/2010 | Fraden | |
| 2010/0298724 A1 | 11/2010 | Vivenzio et al. | |
| 2010/0298725 A1 * | 11/2010 | Vivenzio | A61B 5/02233 600/490 |
| 2011/0071410 A1 | 3/2011 | Chul | |
| 2011/0160599 A1 | 6/2011 | Kobayashi et al. | |
| 2015/0216430 A1 | 8/2015 | Quinn et al. | |

OTHER PUBLICATIONS

Miyauchi, Machine Translation of JP 1 014892A, 1998, Japanese Patent Office Office.

Office Action for U.S. Appl. No. 14/687,335, dated Jan. 4, 2016, Quinn et al., "Blood Pressure Cuff", 19 pages.

Office Action for U.S. Appl. No. 13/220,314, dated Oct. 23, 2014, Quinn et al., "Blood Pressure Cuff", 14 pages.

Office Action for U.S. Appl. No. 13/220,314, dated Apr. 16, 2014, Quinn et al., "Blood Pressure Cuff", 9 pages.

Office Action for U.S. Appl. No. 14/687,335, dated Aug. 7, 2015, Quinn et al., "Blood Pressure Cuff", 11 pages.

* cited by examiner

BLOOD PRESSURE CUFF

CROSS-REFERENCE TO RELATED APPLICATIONS

This Application is a continuation of U.S. patent application Ser. No. 14/687,335, entitled "Blood Pressure Cuff," filed Apr. 15, 2015, which is a divisional application of U.S. patent application Ser. No. 13/220,314, filed Aug. 29, 2011 (now issued U.S. Pat. No. 9,028,419). The entire disclosures of each of the above applications are incorporated herein by reference.

FIELD OF THE INVENTION

The present disclosure relates to systems and methods for blood pressure determination and, in particular, to systems and methods of determining blood pressure using an inflatable blood pressure cuff.

BACKGROUND OF THE INVENTION

The measurement of blood pressure is a common procedure used in hospitals, clinics, and other health care facilities to assist in diagnosing illnesses and monitoring patient health. In standard non-invasive blood pressure measurement practice, a patient's arterial blood pressure is measured using an inflatable sleeve, commonly referred to as a blood pressure cuff. The cuff is typically adapted to fit around a limb of the patient, and such cuffs are usually sized to fit around the patient's upper arm, between the armpit and the elbow. After placing the cuff around the upper arm, a bladder within the cuff is inflated to occlude the brachial artery, the primary blood vessel in the arm carrying blood away from the heart.

Blood pressure cuffs are typically available in a variety of standard sizes depending on the arm circumference (i.e., neonatal, child, and adult) of the patient. The Association for Advancement of Medical Instrumentation (AAMI) has published standards that suggest bladder dimensions for each of these categories. The AAMI standards indicate, for example, that the adult cuff bladder length should be approximately 0.80 times the circumference of the limb at the midpoint of the intended range of the cuff. This published AAMI standard also states that the width of the adult cuff bladder should be approximately 0.40 times the circumference of the limb at the midpoint of the intended range of the cuff. While these standard cuff ratios may be adequate for the majority of patients, such standard blood pressure cuffs are not well-suited for patients having arms with abnormally large circumferences.

Obese and/or muscular patients, for example, typically have arms with circumferences that are much larger than an average patient. In addition, for most obese patients, the distance between the armpit and the elbow is relatively short as compared to the arm circumference. Such arm geometry can pose challenges to health care providers when trying to properly occlude the brachial artery during non-invasive blood pressure readings. For instance, although obese patients may require blood pressure cuffs longer than the standard blood pressure cuffs described above to account for the circumference of their arms, the AAMI standards stipulate that the width of such a cuff bladder must increase as the length of the bladder increases. For most obese patients, however, the distance between the elbow and the armpit is typically not long enough to accommodate a blood pressure cuff with the stipulated increased width. Thus, while a blood pressure cuff sized for such patients may have a length adequate to encircle the circumference of the patient's arm, the width of such a cuff would extend beyond the patient's elbow. Under such a scenario, the bone structure of the elbow would hinder occlusion of the brachial artery during inflation of the cuff, causing blood pressure readings to be inaccurate. Also, covering the anticubital fasa makes the proper placement of a stethoscope impossible for a traditional manual blood pressure cuff reading.

Conversely, while it may be possible to construct a conventional single-bladder blood pressure cuff having a length sufficient to encircle such large circumference arms and a width sufficient to fit between the armpit and the elbow, such a hypothetical blood pressure cuff would inflate to have an undesirably narrow cross-section along the length of the arm before achieving the pressure required to occlude the brachial artery of obese patients. Generally, approximately 3 inches of cuff contact width is required between the armpit and the elbow for accurate blood pressure measurements during occlusion of the brachial artery. Thus, the width of such hypothetical cuffs would not maintain sufficient contact with the arm of the patient during occlusion, and blood pressure measurements obtained using such cuffs would also be prone to error.

The exemplary embodiments of the present disclosure are directed toward overcoming the deficiencies described above.

SUMMARY

In an exemplary embodiment of the present disclosure, a blood pressure cuff includes a first bladder having a width, and a length transverse to the width. The blood pressure cuff also includes a second bladder connected to the first bladder and a port fluidly connected to at least one of the first and second bladders.

In another exemplary embodiment of the present disclosure, a blood pressure cuff includes a first bladder including a top sealed to a bottom opposite the top. The first bladder includes a width, and a length equal to approximately three times the width. The blood pressure cuff also includes a second bladder fluidly connected to the first bladder. The second bladder includes a top sealed to the bottom of the first bladder, and a bottom sealed to the top of the second bladder. The second bladder includes a length and a width approximately equal to the respective length and width of the first bladder. The blood pressure cuff further includes a port sealed to the top of the first bladder. The port is fluidly connected to the first bladder.

In a further exemplary embodiment of the present disclosure, a blood pressure cuff includes a bladder having a length and a variable width, the variable width including a maximum width and a minimum width. The bladder includes a first wall, a second wall opposite the first wall, and a plurality of partitions extending from the first wall to the second wall. Each partition of the plurality of partitions includes a plurality of thru holes and a band. The band restricts lateral expansion of the bladder beyond the maximum width.

In an additional exemplary embodiment of the present disclosure, a blood pressure cuff includes a connection portion including a tail, and an inflation portion connected to the connection portion, the inflation portion including a pocket, and a top having an orifice. The blood pressure cuff also includes an inflatable bladder removably disposed within the pocket. The inflatable bladder includes a port passing through the orifice.

DETAILED DESCRIPTION

Figure 1:
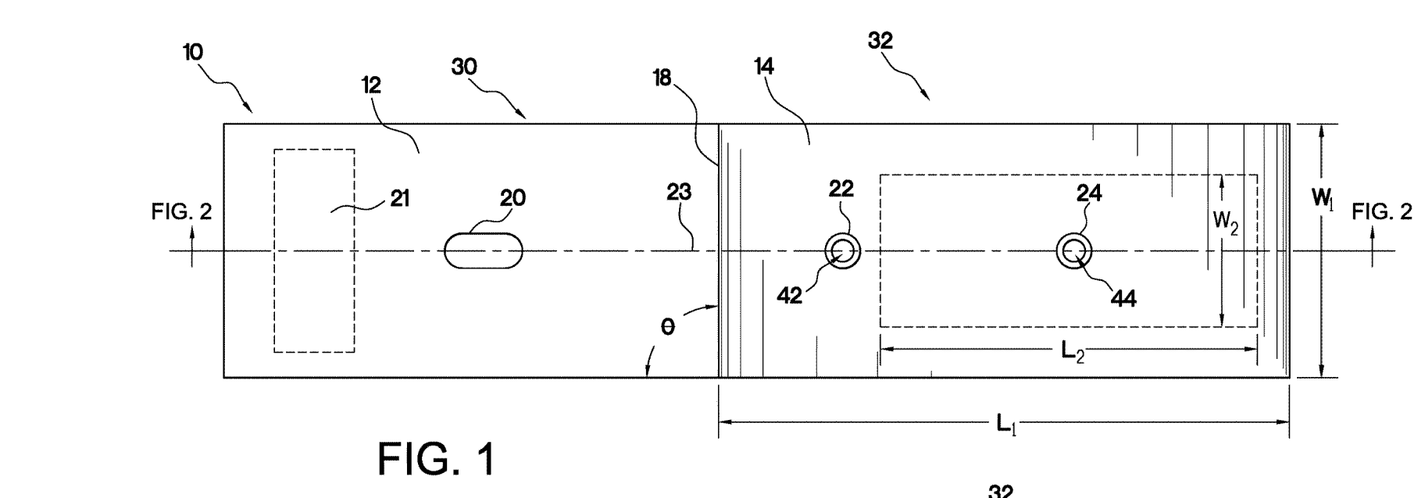
FIG. 1 illustrates a blood pressure cuff according to an exemplary embodiment of the present disclosure.
Figure 2:
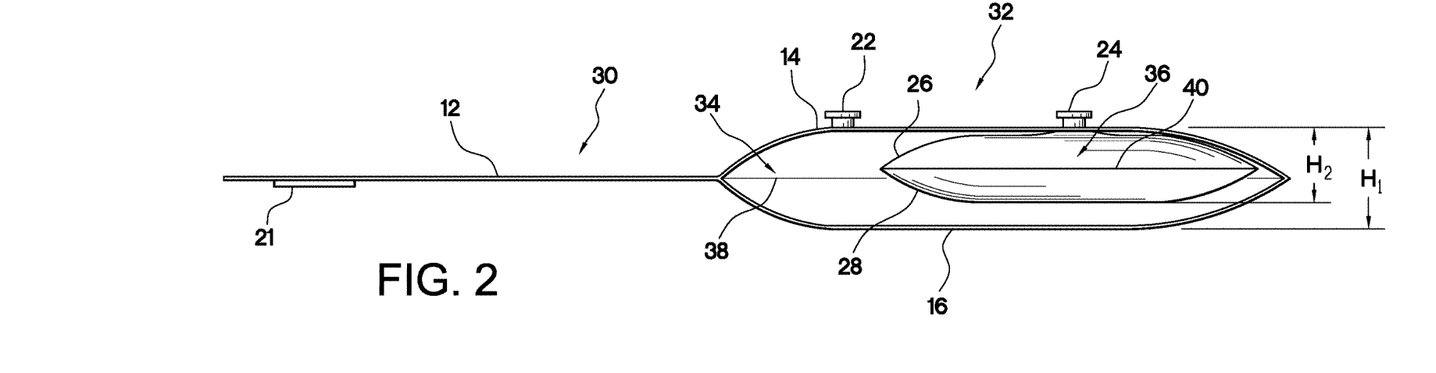
FIG. 2 is a cross-sectional view of the exemplary blood pressure cuff shown in FIG. 1.

FIG. 1 illustrates an exemplary blood pressure cuff 10 of the present disclosure. The blood pressure cuff 10 includes an inflatable portion 32 and a connection portion 30 connected to the inflatable portion 32. As shown in FIG. 2, the inflatable portion 32 includes at least one bladder, and in exemplary embodiments, the inflatable portion 32 may include a first inflatable bladder 34 and a second inflatable bladder 36. The first bladder 34 may include a top 14 and a bottom 16 disposed opposite the top 14. Likewise, the second bladder 36 may include a top 26 and a bottom 28 disposed opposite the top 26. Each of the bladders 34, 36 may be formed from a single piece of material or, alternatively, at least one of the bladders 34, 36 may be formed from separate pieces of material that are joined together through heat sealing, ultrasonic or RF welding, adhering, and/or other processes. In exemplary embodiments in which at least one of the bladders 34, 36 is formed from a single piece of material, the piece of material may be folded along a seam 38,40 to form the top 14,26 and the bottom 16, 28. In such exemplary embodiments, a remaining perimeter of the piece of material may be sealed opposite the seams 38, 40 to form a substantially fluid tight bladder 34, 36.

Alternatively, in exemplary embodiments in which at least one of the bladders 34, 36 is formed from separate pieces of material, the top 14,26 of the bladder 34, 36 may comprise a first panel, and the bottom 16, 28 of the bladder 34, 36 may comprise a separate second panel. In such exemplary embodiments, the first panel may be sealed to the second panel about a perimeter of the respective panels to form a substantial fluid tight bladder 34, 36. For example, each bladder of the present disclosure may be formed from separate sheets and/or panels of material, and sealed along respective peripheral edges thereof.

The blood pressure cuffs of the present disclosure may be formed from any medically approved material known in the art. Such materials may be highly flexible, durable, and suitable for contact with, for example, the skin of a patient. Such materials may also be tear-resistant, fluid-impermeable, and recyclable. Such materials may include, for example, paper, cloth, mesh and/or polymers such as polypropylene or polyethylene. In still further exemplary embodiments, such materials may be coated and/or otherwise treated with one or more additives that cause the material to become biodegradable within a desired time interval (e.g., within 2 to 3 months).

Each of the exemplary bladders described herein may have a respective length, width, and inflated height suitable for use with obese patients. For example, as shown in FIGS. 1 and 2, the first bladder 34 may have a deflated length L1 and a deflated width W1, and the second bladder 36 may have a respective corresponding deflated length L2 and deflated width W2. Unless otherwise indicated, the lengths and widths referred to for the duration of this disclosure are intended to be deflated lengths and widths. In exemplary embodiments, inflated lengths and widths of the exemplary bladders described herein may be different than the corresponding deflated lengths and widths.

In an exemplary embodiment, the second bladder 36 may be disposed within the first bladder 34. In such exemplary embodiments, the length L2 and width W2 of the second bladder 36 may each be less than the corresponding length L1 and width W1 of first bladder 34. At least one of the bladders 34, 36 may have a length L1, L2 sufficient to completely encircle a circumference of an obese patient's arm. In such exemplary embodiments, at least one of the lengths L1, L2 may be up to approximately 30 inches or greater. In further exemplary embodiments, at least one of the lengths L1, L2 may be greater than approximately 11 inches, such as between approximately 11 inches and approximately 16 inches. In still further exemplary embodiments, at least one of the lengths L1, L2 may be between approximately 11.25 inches and approximately 13.7 5 inches. It is also contemplated that in other exemplary embodiments, at least one of the lengths L1, L2 may be between approximately 2 inches and approximately 4 inches. In addition, in any of the exemplary embodiments described herein, at least one of the widths W1, W2 may be sufficient to extend between the armpit and the elbow of the obese patient's arm. In such exemplary embodiments, at least one of the widths WI, W2 may be less than approximately 8 inches. In further exemplary embodiments, at least one of the widths W1, W2 may be between approximately 5 inches and approximately 7 inches. In further exemplary embodiments, at least one of the widths W1, W2 may be between approximately 5.25 inches and approximately 6.5 inches.

As shown in FIG. 2, in an inflated state, the first bladder 34 may have a height H1, and the second bladder 36 may have a height H2 that is less than the height H1. When fully inflated, the height H1 may be between approximately 5 inches and approximately 6 inches. Although the height H2 of the inflated second bladder 36 may be less than the height H1 of the inflated first bladder 34, in exemplary embodiments, both bladders 34, 36 may be inflated to assist in occluding the brachial artery of the patient during blood pressure measurement. In further exemplary embodiments, however, the first bladder 34 may be inflated for occlusion of the brachial artery of obese patients, while the second bladder 36 may be inflated for occlusion of the brachial artery of non-obese patients. At least one of the first and second bladders 34, 36 may be inflatable to a pressure of approximately 160 mm Hg to assist in occluding the brachial artery of such patients.

The blood pressure cuff 10 may further include a first port 22 fluidly connected to the first bladder 34, and a separate second port 24 fluidly connected to the second bladder 36. Each of the bladders 34, 36 may include an orifice configured to accept at least a portion of the respective port 22, 24. For example, at least a portion of each port 22, 24 may pass through a respective orifice of the bladders 34, 36 so as to provide a fluid passage 42, 44 into and out of the respective bladders 34, 36. In further exemplary embodiments, at least a portion of the respective port 22, 24 may be sealed to the respective bladders 34, 36 about a perimeter of the orifice. The ports 22, 24 may be sealed to the bladders 34, 36 by, for example, heat sealing, ultrasonic or RF welding, adhering, and/or any other process known in the art. In an exemplary embodiment, the top 14, 26 of each bladder 34, 36 may define such an orifice, and each port 22, 24 may be fluidly and/or mechanically connected to the top 14, 26 of each bladder 34, 36 about the perimeter of such orifices.

In the exemplary embodiments of FIGS. 1 and 2, the first bladder 34 may include two such orifices. The first port 22 may be sealed to the first bladder 34 about a perimeter of the first orifice, and the second port 24 may be sealed to the first bladder 34 about a perimeter of the second orifice. Additionally, the second bladder 36 may include a single orifice. The second bladder 36 may be sealed and/or otherwise connected to the first bladder 34 about a perimeter of the single orifice. The single orifice of the second bladder 36 and the second orifice of the first bladder 34 may be substantially aligned to facilitate such a connection. In addition, the second port 24 may be sealed to the first and second bladders 34, 36 about the respective perimeters of these orifices.

In exemplary embodiments, each port 22, 24 may comprise an open-ended cylindrical cavity. A portion of the port 22, 24 may protrude from the top 14, 26 of each respective bladder 34, 36, and may include, for example, a circumferential shelf, flange, ridge, and/or other like structure to facilitate connection with one or more known inflation devices. For example, the port 22, 24 may be shaped, sized, and/or otherwise configured to mate with a corresponding pump, bulb, gauge, hose, adapter, fitting, and/or other device utilized by a health care professional to inflate the corresponding bladder 34, 36 and/or measure patient blood pressure. As a result, the port 22, 24 may enable fluid as well as mechanical connection with inflation and/or blood pressure measurement devices known in the art. For example, such ports 22, 24 may facilitate connection with one or more hand operated inflation bulbs by way of a releasable fitting. Additional details concerning exemplary port designs are provided in co-owned U.S. Pat. No. 6,422,086, entitled "Low Profile Pressure Measuring Device," the entire disclosure of which is incorporated herein by reference.

The connection portion 30 may be connected to the inflatable portion 32 along a seam 18 through heat sealing, ultrasonic or RF welding, adhering, and/or any of the processes described above. In additional exemplary embodiments, the connection portion 30 may be formed from the same piece of material as either the top 14 or the bottom 16 of the first bladder 34. In such exemplary embodiments, the seam 18 may be omitted. While FIG. 1 illustrates the connection portion 30 extending substantially linearly from the inflatable portion 32, in additional exemplary embodiments, the connection portion 30 may extend from the inflatable portion 32 at any desired angle 8. In exemplary embodiments, the angle 8 may be between approximately 60 degrees and approximately 90 degrees depending upon the geometry of the patient's arm. In still further exemplary embodiments, the blood pressure cuff 10 may be curved, rounded, and/or otherwise substantially arcuate in shape. In such exemplary embodiments, the top 14 and bottom 18 of the first bladder 34 may be formed from the same piece of material as the connection portion 30, and the entire blood pressure cuff 10 may be cut and/or otherwise formed to have any desired arcuate shape and/or radius.

The connection portion 30 may include a tail 12, a slot 20, and a connector 21. The slot 20 may extend along a central longitudinal axis 23 of the blood pressure cuff 10, and in an exemplary embodiment, the slot 20 may be aligned with the ports 22, 24. The slot 20 may have a width transverse to the longitudinal axis 23 that is sized to accept passage of the ports 22, 24 therethrough. The slot 20 may also have a longitudinal length that limits the effective circumference of the blood pressure cuff 10. In exemplary embodiments, the slot 20 may have a length between approximately 5 inches and approximately 6 inches, and such a length may yield a maximum blood pressure cuff circumference of approximately 19 inches and a minimum blood pressure circumference of approximately 15 inches. In such exemplary embodiments, both of the ports 22, 24 may extend through the slot 20 when the blood pressure cuff 10 is worn by the patient.

In further exemplary embodiments, the length of the slot 20 may be between approximately 1 inch and approximately 3 inches. In such exemplary embodiments, only one of the ports 22, 24 may extend through the slot 20 when the blood pressure cuff 10 is worn by the patient, while the tail 12 may overlay the other of the ports 22, 24. Alternatively, in embodiments in which only one of the ports 22, 24 may extend through the slot 20 when the blood pressure cuff 10 is worn by the patient, an end of the tail may be disposed between the ports 22, 24 during use. For example, the slot 20 may be sized such that only one of the ports 22, 24 extends therethrough when the blood pressure cuff 10 is used on an arm of standard circumference, and the other of the ports 22, 24 may extend therethrough when the blood pressure cuff 10 is used on an arm having, for example, a relatively large circumference. In this way, the length and/or other configurations of the slot 20 may ensure that the proper port 22, 24 is used depending on the circumference of the individual patient's arm. As a result, the range of arm sizes (i.e., circumferences) that the blood pressure cuff 10 can be used with is limited by the length of the slot 20.

In exemplary embodiments, the tail 12 may be configured to encircle at least 75 percent of the first bladder 34 when the blood pressure cuff 10 is wrapped around and/or otherwise worn on an arm of the patient. In further exemplary embodiments, the tail 12 may be configured to encircle greater than 100 percent of the first bladder 34 when the blood pressure cuff 10 is worn, and in such exemplary embodiments, the tail 12 may have a length greater than the length L1 of the first bladder 34.

The connector 21 may include any known adhesive, hook, loop, fastener, clip, snap, tie, and/or other like releasable connection device. In further exemplary embodiments, the connector 21 may include one or more patches of Velcro® connected to the tail 12. In such exemplary embodiments, the connector 21 may be disposed on an underside of the tail 12, and the connector 21 may be configured to releasably attach to the top 14 of the first bladder 34 and/or a topside of the tail 12 while the blood pressure cuff 10 is worn on the arm of the patient.

While the exemplary blood pressure cuff 10 illustrated in FIGS. 1 and 2 includes a second bladder 36 disposed within and fluidly separate from the first bladder 34, additional exemplary blood pressure cuffs of the present disclosure may include one or more second bladders outside of and fluidly connected to the first bladder 34. For example, FIGS. 3 and 4 illustrate a blood pressure cuff 100 according to an additional embodiment of the present disclosure, wherein the blood pressure cuff 100 includes a first bladder 34, and a second bladder 46 fluidly connected to the first bladder 34.

The second bladder 46 may include a top 48 and a bottom 50 disposed opposite the top 48. In exemplary embodiments, at least one of the first and second bladders 34, 46 may be formed from a single piece of material. In such exemplary embodiments, the single piece of material may be folded along a seam 38, 52 to form the top 14, 48 and the bottom 16, 50. In further exemplary embodiments, at least one of the first and second bladders 34, 46 may be formed from separate pieces of material. In such exemplary embodiments, the top 14 of the first bladder 34 may comprise a first panel and the bottom 16 may comprise a separate second panel. In addition, the top 48 of the second bladder 46 may comprise a third panel and the bottom 50 may comprise a separate fourth panel. In such exemplary embodiments, the separate panels of material may be sealed along respective perimeters thereof to form the first and second bladders 34, 46.

The bottom 16 of the first bladder 34 may include a plurality of orifices 55. Although FIGS. 3 and 4 illustrate three such orifices 55, in additional exemplary embodiments, the bottom 16 may include more than or less than three orifices 55 depending upon the application and the desired inflation characteristics of the blood pressure cuff 100. In addition, although the orifices 55 are shown as being substantially aligned along the central longitudinal axis 23 of the first bladder 34, in additional exemplary embodiments, the orifices 55 may be disposed at any alternative location along the bottom 16 to facilitate inflation of the first and second bladders 34, 46. Further, although FIG. 4 illustrates the orifices 55 having respective centerlines that are offset from a centerline of the port 22, in further exemplary embodiments, at least one of the orifices 55 may have a centerline that is substantially collinear with the centerline of the port 22.

Figure 3:
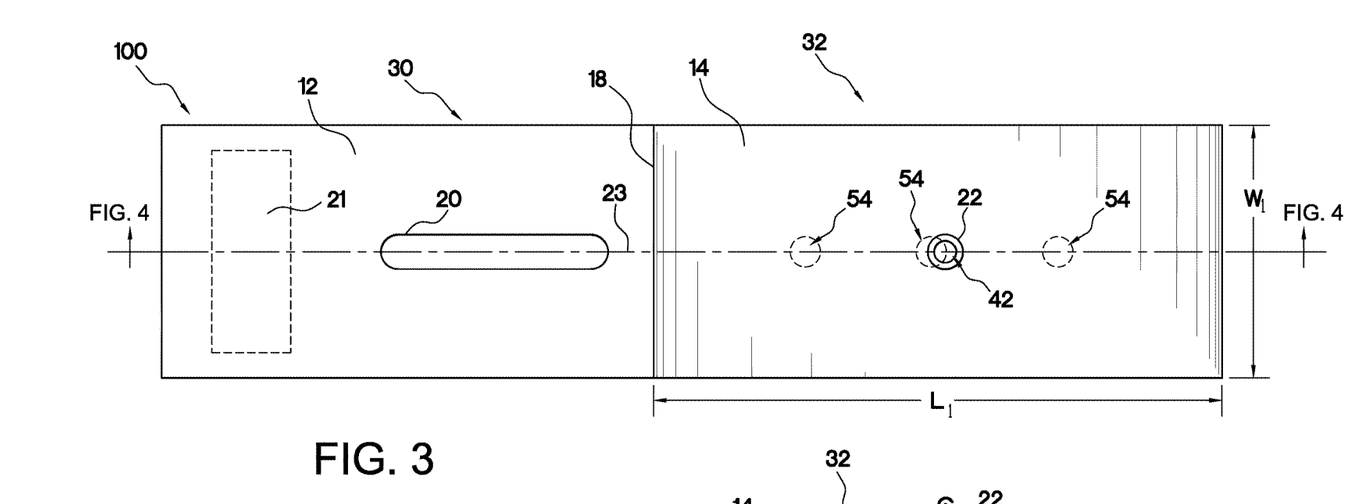
FIG. 3 illustrates a blood pressure cuff according to another exemplary embodiment of the present disclosure.
Figure 4:
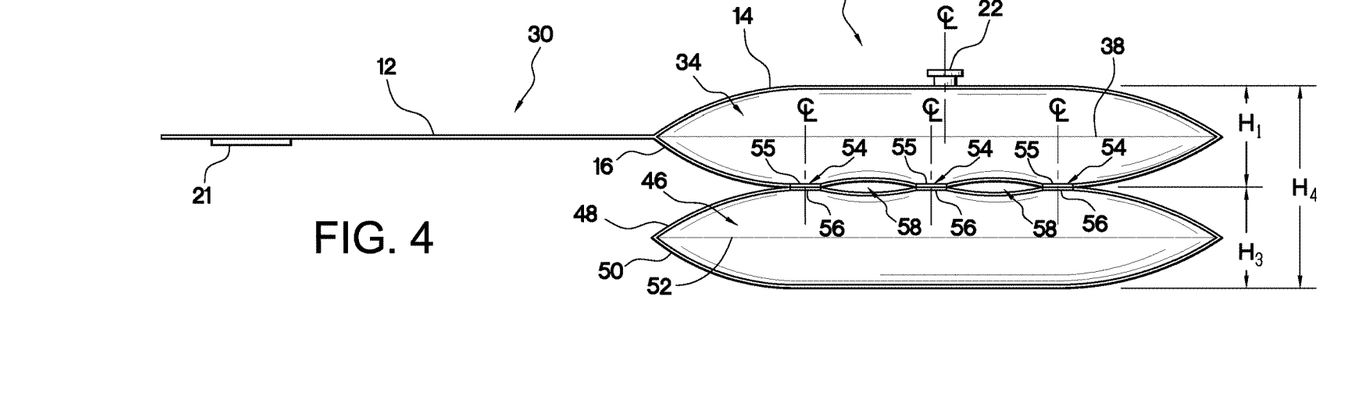
FIG. 4 is a cross-sectional view of the exemplary blood pressure cuff shown in FIG. 3.

As shown in FIGS. 3 and 4, the top 48 of the second bladder 46 may also include a plurality of orifices 56. The shape, size, and/or location of the orifices 56 may substantially correspond to the shape, size, and/or location of the orifices 55. In exemplary embodiments, the orifices 55, 56 may permit the passage of fluids such as, for example, compressed air, between the first and second bladders 34, and 46. In particular, a perimeter of each orifice 55 may be sealed to a perimeter of a corresponding orifice 56 of the second bladder 46. The sealed orifices 55, 56 may define respective passages 54 extending between the first and second bladders 34, 46. In exemplary embodiments, the bottom 16 of the first bladder 34 may be sealed to the top 48 of the second bladder 46 about a respective perimeter of each of the orifices 55. Likewise, the top 48 of the second bladder 46 may be sealed to the bottom 16 of the first bladder 34 about a respective perimeter of each of the orifices 56. In such exemplary embodiments, a separate passage 54 may be formed at each of the sealed orifices 55, 56. Moreover, the blood pressure cuff 100 may include a gap 58 disposed between each of the passages 54. At such gaps 58, the top 48 may lie substantially adjacent to the bottom 16.

In exemplary embodiments, the first and second bladders 34, 46 illustrated in FIGS. 3 and 4 may have substantially the same dimensions. For example, a width of the second bladder 46 may be approximately equal to a width of the first bladder 34, and a length of the second bladder 46 may be approximately equal to a length of the first bladder 34. In such exemplary embodiments, the first and second bladders 34, 46 may have substantially the same length L1 and width W1 described above with regard to the first bladder 34 of the blood pressure cuff 10. For example, the width W1 of the first and second bladders 34, 46 may be less than approximately 6 inches, and in further exemplary embodiments, the width W1 may be between approximately 5 inches and approximately 6 inches. In such exemplary embodiments, at least 3 inches of the width W1 of the second bladder 46 may be configured to maintain contact with an arm of the patient while the blood pressure cuff 100 occludes the brachial artery of the patient. In addition, the first bladder 34 may be inflatable to a height H1, and the second bladder 46 may be inflatable to a height H3 that is substantially equal to the height H1 of the first bladder 34. In exemplary embodiments, the first and second bladders 34, 46 may be inflatable to a combined height H4 between approximately 5 inches and approximately 6 inches.

In such exemplary embodiments, the first bladder 34 may be inflated to any desired inflation pressure suitable for occluding the brachial artery of an obese patient, and the second bladder 46 may be inflatable to an inflation pressure that is approximately equal to the inflation pressure within the first bladder. In such exemplary embodiments, the first and second bladders 34, 46 may be inflatable up to approximately 100 mm Hg or more. In such exemplary embodiments, the first and second bladders may be inflatable to an inflation pressure of approximately 160 mm Hg. In order to achieve such inflation pressures, the first and second bladders 34, 46 may have any of the lengths L1 and/or widths W1 described herein, and in an exemplary embodiment the first bladder 34 may have a width W1, and a length L1 equal to approximately three times the width W1. In addition, although the first and second bladders 34, 46 have been described herein as having approximately equal dimensions, in further exemplary embodiments, the length, width, and/or inflated height of the second bladder 46 may be different than the corresponding length, width, and/or inflated height of the first bladder 34. In addition, while the first and second bladders 34, 46 have been described herein as having a substantially rectangular shape, in additional exemplary embodiments, at least one of the first and second bladders 34, 46 may be crescent-shaped, horn shaped, conical, spherical, cube-shaped, and/or any other shape known in the art. A shape of the first bladder 34 may be different than a shape of the second bladder 46.

Figures 5, 6:
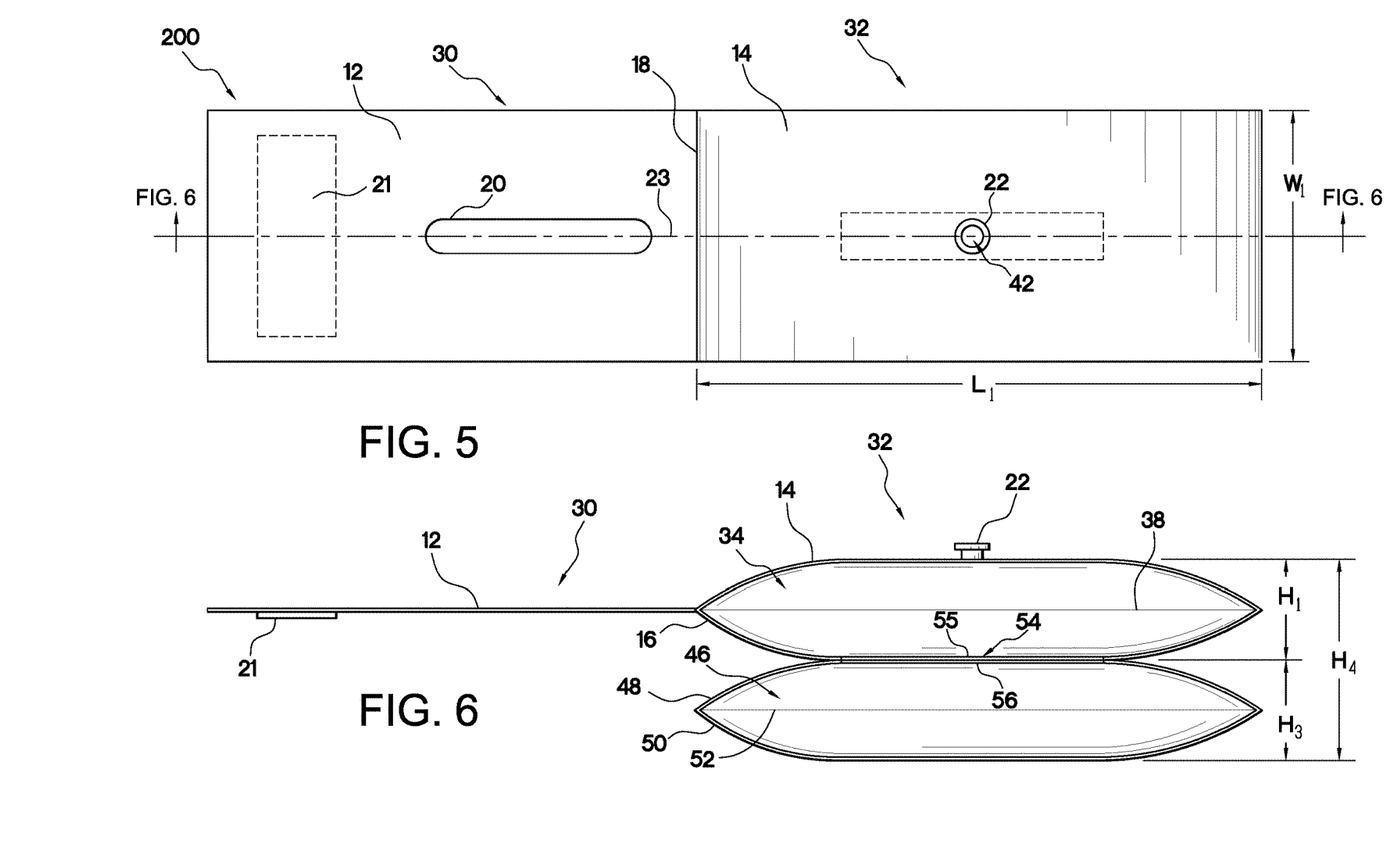
FIG. 5 illustrates a blood pressure cuff according to a further exemplary embodiment of the present disclosure.
FIG. 6 is a cross-sectional view of the exemplary blood pressure cuff shown in FIG. 5.

As shown in FIGS. 5 and 6, in additional exemplary embodiments, the blood pressure cuff 200 may include first and second bladders 34, 46 that are fluidly connected via a single passage 54. For example, the bottom 16 of the first bladder 34 may include an elongated orifice 55, and the top 48 of the second bladder 46 may include a corresponding elongated orifice 56. The corresponding elongated orifices 55, 56 may each be disposed along the central longitudinal axis 23 of the blood pressure cuff 200. As described above with regard to the orifices 55, 56 shown in FIG. 4, the bottom 16 of the first bladder 34 may be sealed to the top 48 of the second bladder 46 about a perimeter of the elongated orifice 55, likewise the top 48 of the second bladder 46 may be sealed to the bottom 16 of the first bladder 34 about a perimeter of the elongated orifice 56. The sealed orifices 55, 56 may define a single passage 54, and passage 54 may facilitate fluid communication between the first bladder 34 and the second bladder 46. For example, compressed air and/or other like fluids may be provided to the first bladder 34 via the port 22, and such fluids may flow from the first bladder 34 to the second bladder 46 via the passage 54.

The length, width, location, and/or other configurations of the corresponding elongated orifices 55, 56 may assist in maintaining an inflation pressure within the first bladder 34 that is substantially equal to an inflation pressure within the second bladder 46 while occluding a brachial artery of the patient. For example, the orifices 55, 56 may have a maximum longitudinal length that is at least two thirds as long as the length L1 of the first bladder 34. Likewise, the elongated orifices 55, 56 may have a maximum width transverse to the longitudinal axis 23 that is at least one half the width W1 of the first bladder 34. While FIG. 5 illustrates the passage 54 formed by the orifices 55, 56 as having a substantially rectangular shape, in additional exemplary embodiments, the passage 54 may be oblong, ovular, and/or any other shape useful in facilitating the inflation of the blood pressure cuff 200. In such exemplary embodiments, the shape of the passage 54 may correspond to the shape of the corresponding elongated orifices 55, 56, and the shape of the passage 54 may be different than the shape of, for example, at least one of the first and second bladders 34, 46.

As illustrated in FIGS. 11-14, in additional exemplary embodiments, a blood pressure cuff 400, 500 of the present disclosure may include one or more removable, separable, and/or detachable bladders 34. For example, the blood pressure cuff 400 shown in FIGS. 11 and 12 may include one or more pockets 90 configured to accept an inflatable bladder 34. The pocket 90 may include a substantially closed front 106 and a substantially open back 108. The back 108 may include an opening sized to accept a deflated and/or partially inflated bladder 34. In such embodiments, the back 108 may also include one or more flaps, clasps, ties, connectors, hooks, buttons, zippers, fittings, and/or other like structures to assist in at least partially retaining the bladder 34 within the pocket 90 during use. In further exemplary embodiments, the back 108 may be fully open.

Figure 11:
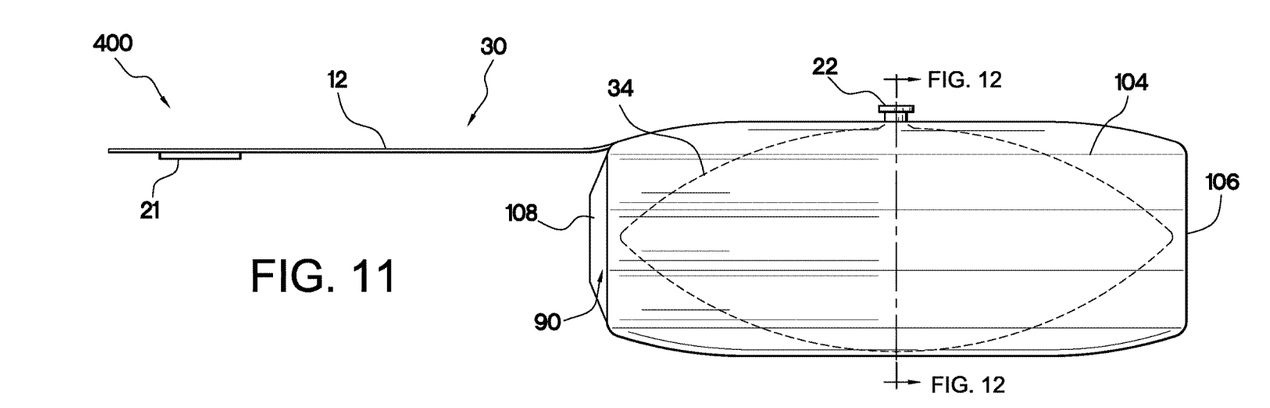
FIG. 11 illustrates a blood pressure cuff according to another exemplary embodiment of the present disclosure.
Figure 12:
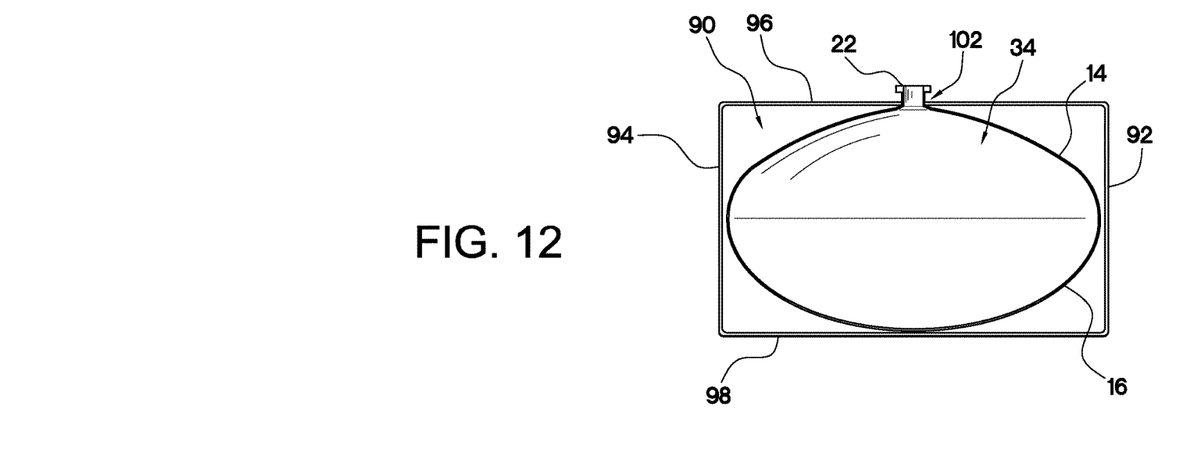
FIG. 12 is a cross-sectional view of the exemplary blood pressure cuff shown in FIG. 11.

The pocket 90 may also include a top 96, and a bottom 98 opposite the top 96. The tail 12 of the blood pressure cuff 400 may be connected to and/or may extend from the top 96, and as shown in FIG. 12, the top 96 may include at least one orifice 102. The orifice 102 may be disposed along a central longitudinal axis of the blood pressure cuff 400, and the orifice 102 may be shaped, sized, and/or otherwise configured to accept passage of a port 22 of the inflatable bladder 34 therethrough. For example, once the bladder 34 has been at least partially disposed within the pocket 90, the port 22 may be passed through the orifice 102 from within the pocket 90. The bladder 34 may then be inflated by, for example, passing pressurized air through the port 22 from outside of the pocket 90 while the bladder 34 is disposed within the pocket 90.

The pocket 90 may further include a pair of opposing sides 92, 94. The sides 92, 94 may be connected to the front 106, top 96, and/or bottom 98 through any of the methods described above. At least one of the sides 92, 94 may include one or more flexible and/or expandable pleats 104. Such pleats 104 may comprise folds allowing for expansion of the pocket 90 as the bladder 34 is inflated. The pocket 90 may be sized to accept bladders 34 having different shapes and sizes therein. For example, the pocket 90 may be sized to accept bladders configured for use with patients having arms of average and/or standard adult circumference. Such bladders may be similar in shape and/or size as the second bladder 36 described above with respect to FIGS. 1 and 2. The pocket 90 may also be sized to accept bladders configured for use with bariatric patients having arms of above average circumference. Such bladders may be similar in shape and/or size as the first bladder 34 described above with respect to FIGS. 1 and 2.

Figure 13:
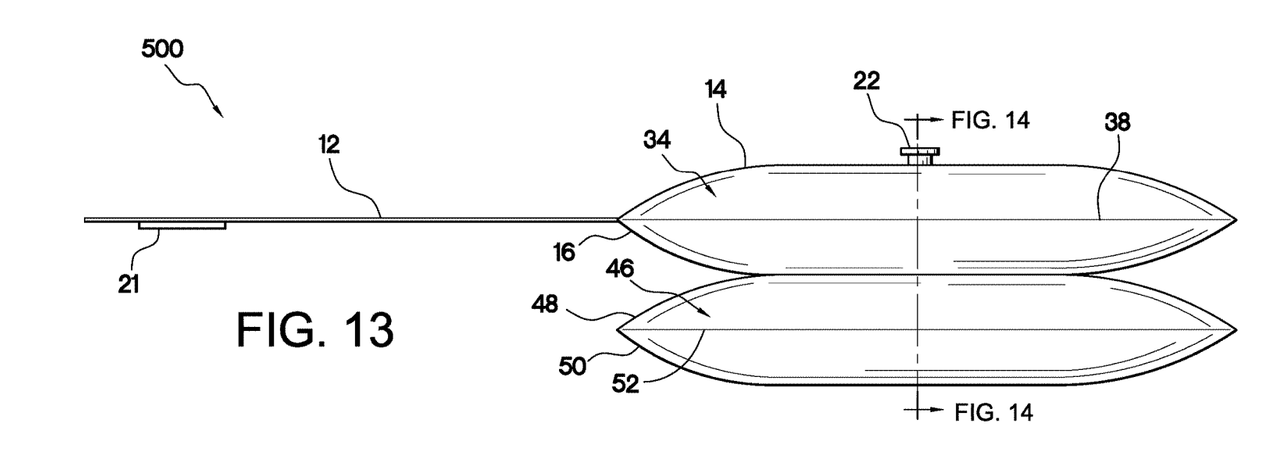
FIG. 13 illustrates a blood pressure cuff according to a further exemplary embodiment of the present disclosure.
Figure 14:
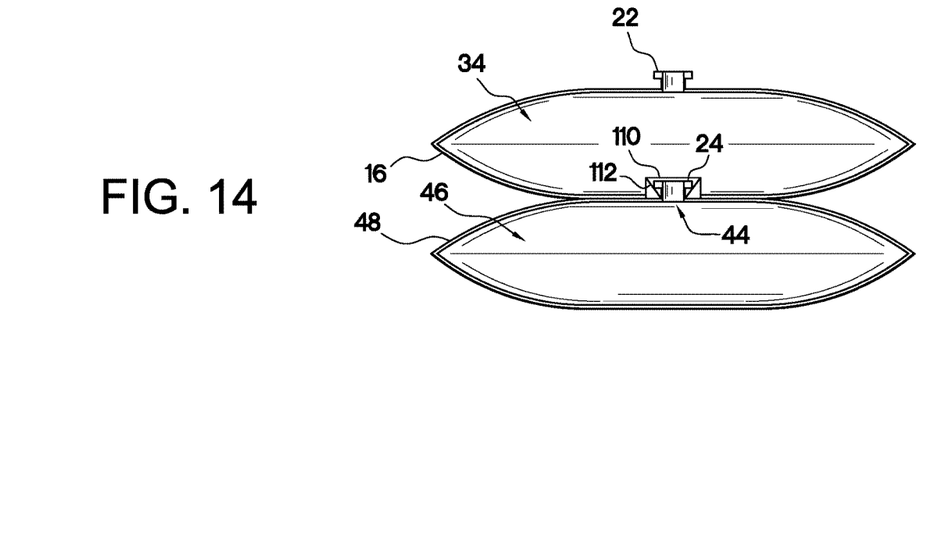
FIG. 14 is a cross-sectional view of the exemplary blood pressure cuff shown in FIG. 13.
Figure 15:
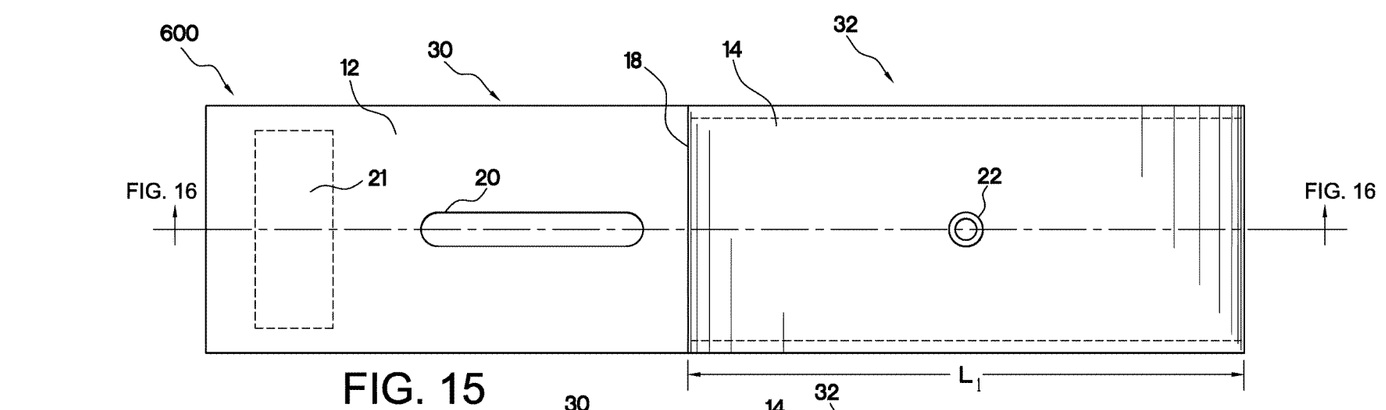
FIG. 15 illustrates a blood pressure cuff according to another exemplary embodiment of the present disclosure.
Figure 16:
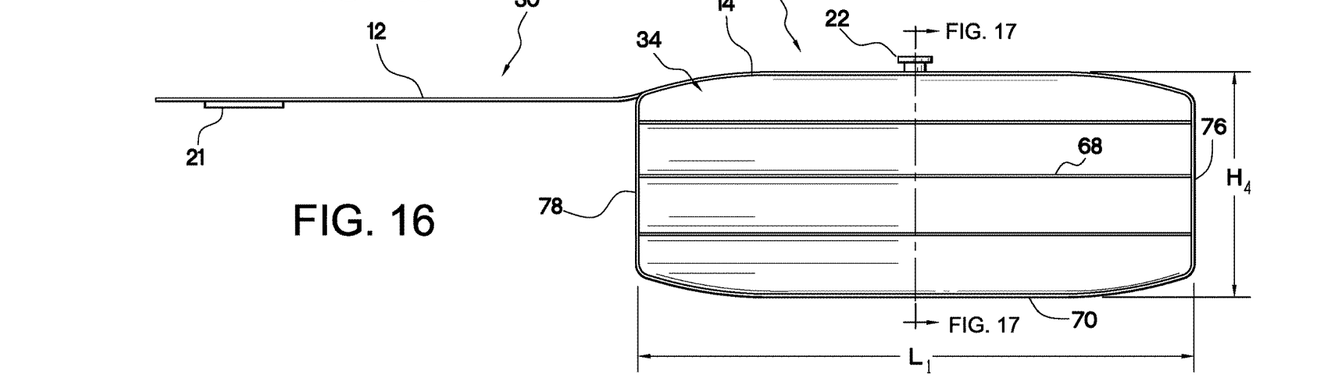
FIG. 16 is a cross-sectional view of the exemplary blood pressure cuff shown in FIG. 15.

As shown in FIGS. 13 and 14, in further exemplary embodiments, the blood pressure cuff 500 may include a first bladder 34, and a second bladder 46 removably attachable to the first bladder 46. For example, the first bladder 34 may include a fitting 110 on the bottom 16 thereof, and the fitting 110 may assist in forming a removable mechanical and/or fluid connection between the bladders 34, 46. The fitting 110 may be, for example, any threaded, snap-on, and/or other type of connector known in the art useful in facilitating a substantially fluid-tight connection. For example, such a fitting 110 may include one or more gaskets 112 forming a fluid-tight seal at the bottom 16 when the second bladder 46 is not connected to the first bladder 34. Upon removably attaching the second bladder 46 to the first bladder 34 by inserting the port 24 into the fitting 110, the fluid-tight seal formed by the gasket 112 at the bottom 16 may be broken. For example, inserting the port 24 into the fitting 110 may temporarily and/or permanently breach the gasket 112. When the port 24 is inserted into the fitting 110, the gasket 112 may assist in retaining the port 24 substantially within the bladder 34, and may facilitate a fluid connection between the first and second bladders 34, 46. For example, the port 24 may form a fluid passage 44 between the first and second bladders 34, 46. In exemplary embodiments, upon detaching the second bladder 46 from the first bladder 34, the gasket 112 may again form a fluid-tight seal at the bottom 16. In this way, multiple second bladders 46 of different shapes, sizes, and/or other configurations may be removably attached and/or otherwise connected to the first bladder 34, and the first bladder 34 may be used repeatedly with or without one or more second bladders 46.

As shown in FIGS. 7-9 and 15-18, in additional exemplary embodiments of the present disclosure, a blood pressure cuff 300, 600 may include an inflatable bladder 34 having a first wall 60, a second wall 62 opposite the first wall 60, and at least one partition 68 extending from the first wall 60 to the second wall 62. In additional exemplary embodiments, the blood pressure cuff 300, 600 may include a plurality of such partitions 68, and at least two of the partitions 68 may have the same dimensions and/or other configurations. As will be described in greater detail below, the bladder 34 of blood pressure cuff 300, 600 may include a variable width between and/or otherwise defined by the first and second walls 60, 62.

Figure 7:
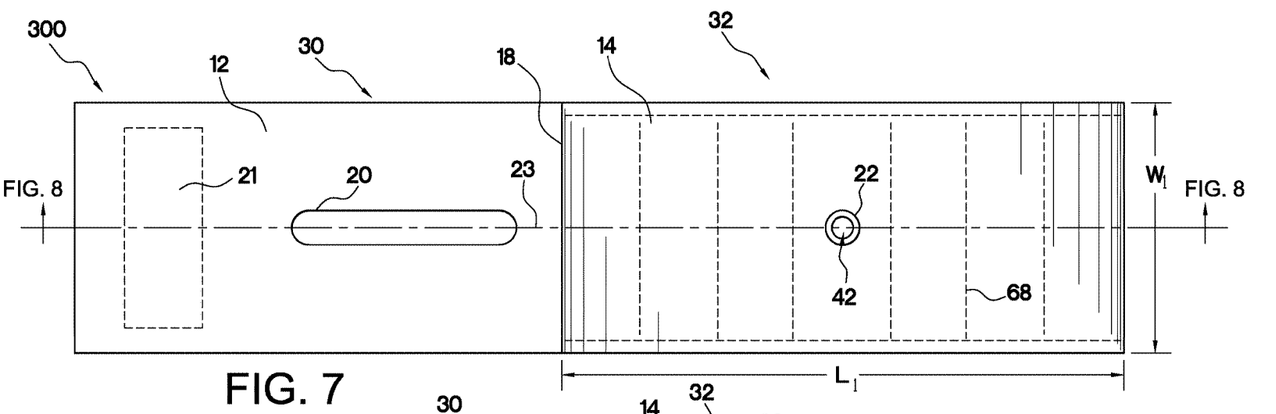
FIG. 7 illustrates a blood pressure cuff according to another exemplary embodiment of the present disclosure.
Figure 8:
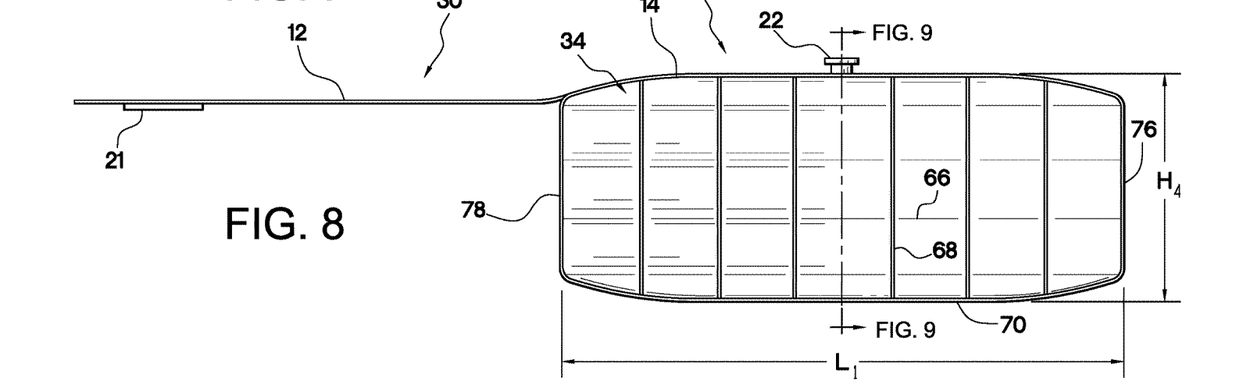
FIG. 8 is a cross-sectional view of the exemplary blood pressure cuff shown in FIG. 7.
Figure 9:
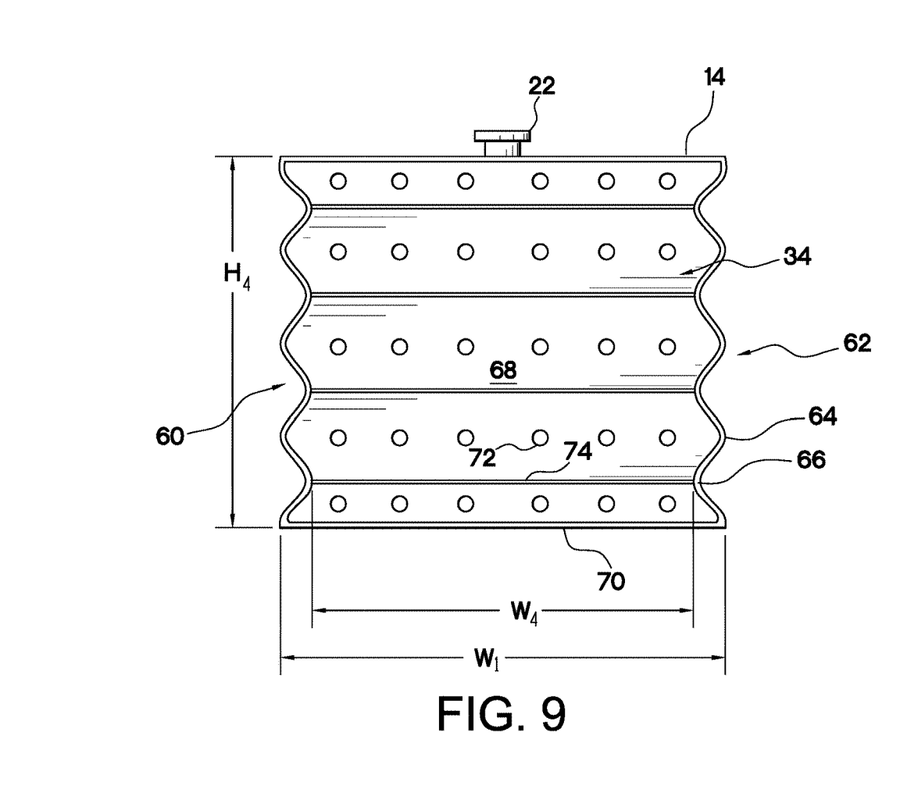
FIG. 9 is a further cross-sectional view of the exemplary blood pressure cuff shown in FIG. 7.

The bladder 34 may also include a front wall 76, and back wall 78 disposed opposite the front wall 76. The bladder 34 may further include a top 14, and a bottom 70 disposed opposite the top 14. The front wall 76 and the back wall 78 may each extend from the top 14 to the bottom 70. In such exemplary embodiments, bladder 34 may be substantially cube-shaped, substantially rectangular, and/or any other known shape. As shown in FIGS. 7-9, at least one of the partitions 68 of the exemplary blood pressure cuff 300 may be disposed substantially parallel to the front and/or back walls 76, 78, and as shown in FIGS. 15-18, at least one of the partitions 68 of the exemplary blood pressure cuff 600 may be disposed substantially parallel the top 14 and/or the bottom 70 of the bladder 34. In further exemplary embodiments, at least one of the partitions 68 may be disposed substantially perpendicular to at least one of the walls 60, 62, the top 14, the bottom 70, the front wall 76, and/or the back wall 78. For example, at least one of the partitions 68 may be disposed substantially parallel to the first wall 60 and/or the second wall 62.

Figures 17, 18, 19:
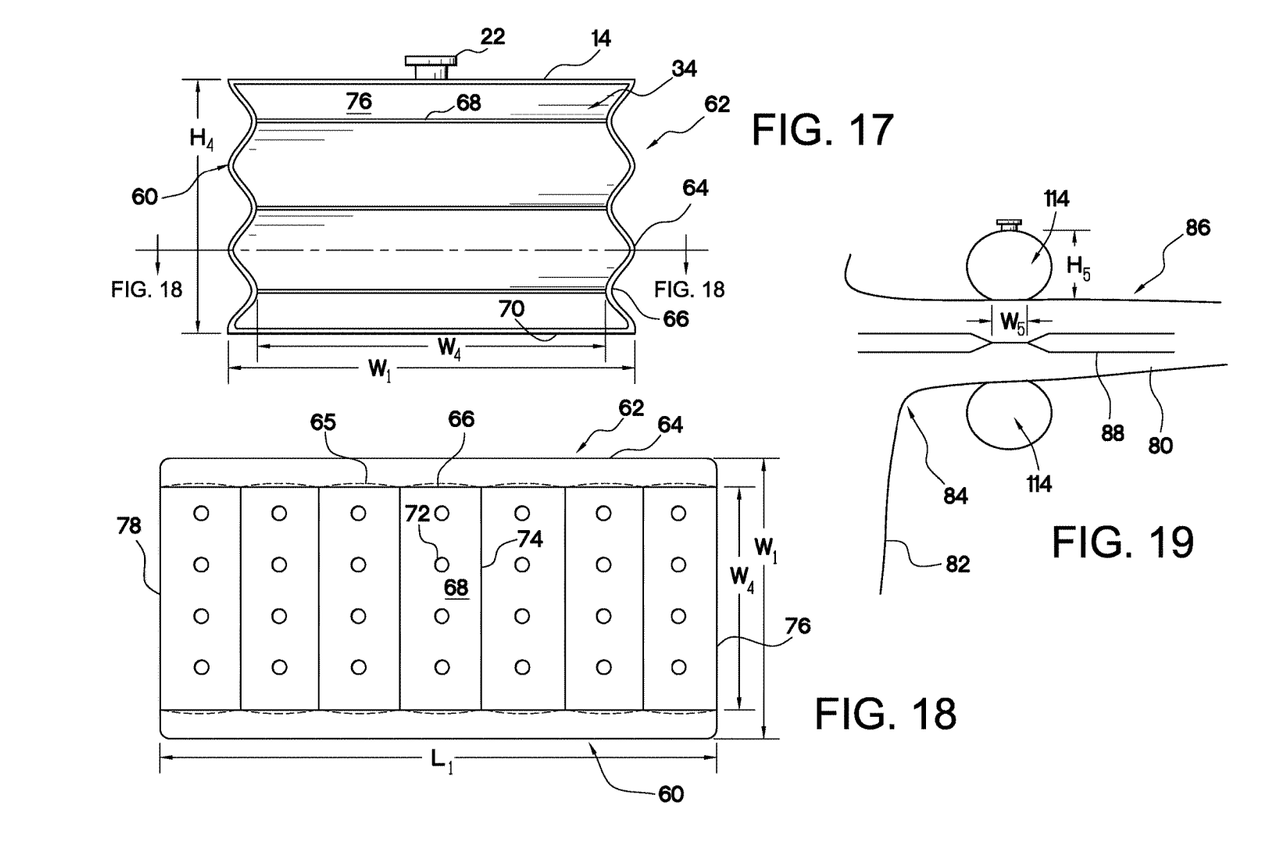
FIG. 17 is a further cross-sectional view of the exemplary blood pressure cuff shown in FIG. 15.
FIG. 18 is another cross-sectional view of the exemplary blood pressure cuff shown in FIG. 15.
FIG. 19 illustrates a conventional blood pressure cuff disposed about a limb of a patient.

As shown in FIGS. 9 and 18, the partition 68 may include a plurality of thru holes 72. Such thru holes 72 may facilitate the passage of fluids between adjacent partitions 68. Each partition 68 may include any number of desired thru holes 72 useful in facilitating the inflation and deflation of the bladder 34. In exemplary embodiments, the size of each thru hole 72 may be inversely related to the number of thru holes 72 included in the partition 68. For example, a partition 68 including thru holes 72 of a relatively large diameter may require fewer thru holes 72 to facilitate the passage of fluid within the bladder 34. The partition 68 may be fanned from, for example, any of the materials described above with regard to the blood pressure cuff 10. For example, the partition 68 may be formed from any flexible, durable, fluid-impermeable material known in the art such as paper, polyethylene, or polypropylene. Such partitions 68 may be connected to, for example, the first and second walls 60, 62 by heat sealing, ultrasonic or RF welding, adhering, and/or any other suitable process. In exemplary embodiments, the partition 68 may not be sealed to, for example, the top 14, bottom 70, front wall 76, and/or back wall 78. In further exemplary embodiments, the partition 68 may be sealed to at least one of the top 14, bottom 70, front wall 76, and/or back wall 78.

The partition 68 may include at least one band 74 disposed along a width thereof. For example, one or more bands 74 may be configured to extend between the first wall 60 and the second wall 62. As shown in FIGS. 9 and 18, the bands 74 may be disposed along a minimum width W4 of the blood pressure cuff 300, 600. For example, the bands 74 may be disposed between a valley 66 of the first wall 60 and a corresponding valley 66 of the second wall 62, and the bands 74 may assist in forming such valleys 66. In the exemplary embodiment of FIGS. 15-18, the partitions 68 may be disposed parallel to the top 14 and/or bottom 70, and may extend between such valleys 66. As shown in phantom in FIG. 18, in such an exemplary embodiment, the first and second walls 60, 62 may form peaks 65 between the adjacent bands 74 when the bladder 34 is inflated due to, for example, the resiliency of the bands 74 relative to the remainder of the partition 68. As a result, at such peaks 65, the bladder 34 may have a localized width greater than the minimum width W4 and less than the maximum width W1.

The bands 74 may be formed from the same material as the partition 68. In additional exemplary embodiments, however, the bands 74 may be formed from material having a greater stiffness, resiliency, and/or rigidity than the material utilized to form the partition 68. Such materials may include, for example, plastic, rubber, polymers and/or other like materials. The bands 74 may be formed integral with and/or may be embedded within the partition 68. Alternatively, the bands 74 may be formed separately from and connected to the partition 68. The greater stiffness, resiliency, and/or rigidity of the bands 74 relative to the partition 68 may assist in restricting lateral expansion of the bladder 34 beyond the maximum width W1 illustrated in FIGS. 9 and 18.

The dimensions of the maximum width WI may correspond to the dimensions of width WI discussed above with regard to the embodiments shown in FIGS. 1, 3 and 5. For example, the bands 74 may restrict expansion of the bladder 34 to a minimum width W4 at each valley 66. Due to this restriction, the bladder 34 may form peaks 64 along the first and second walls 60, 62. In the exemplary embodiment of FIGS. 7-9, such peaks 64 may be formed between each adjacent band 74, and in the exemplary embodiment of FIGS. 15-18, such peaks 64 may be formed between adjacent partitions 68. Such peaks 64 may be disposed adjacent to at least one of the valleys 66 along each wall 60, 62. Thus, in exemplary embodiments, the bladder 34 may have a variable width, and the variable width may include a maximum width WI extending from a peak 64 of the first wall 62 to a corresponding peak 64 of the second wall 62. In addition, as shown in at least FIG. 18, the variable width may include a localized width at each peak 65 that is greater than the minimum width W 4 and less than the maximum width WI. The partition 68 may include any number of bands 74 required to restrict lateral expansion of the bladder 34 in the inflated state. In such exemplary embodiments, the number of bands 74 included in the partition 68 may be directly related to the inflated height H4 or the length LI of the bladder 34. For example, in the exemplary blood pressure cuff 300, a bladder 34 having a greater height H4 may require a greater number of bands 74 to limit expansion of the bladder 34 by locally restricting expansion of the bladder 34 to the minimum width W4. Likewise, in the exemplary blood pressure cuff 600, a bladder 34 having a greater length LI may require a greater number of bands 74 to limit the expansion of the bladder 34 by locally restricting expansion of the bladder 34 to the minimum width W4 and/or to the localized width at each peak 65. In such embodiments, the bands 74 also assist in restricting expansion of the bladder 34 beyond the maximum overall width WI.

The exemplary embodiments of the present disclosure have a variety of advantages over known, single-bladder blood pressure cuffs when measuring the blood pressure of obese or bariatric patients. Such applications are unique from non-obese blood pressure measurement applications due to the enlarged circumference of the patient's arm and the relatively short distance between the patient's armpit and elbow. For instance, a typical obese patient's mm may have a circumference of approximately 14 inches or more. At the same time, the distance between such a patient's armpit and elbow may be between approximately 5 inches and approximately 6 inches. While standard adult blood pressure cuffs having a length sufficient to wrap around an arm having such a circumference, such cuffs may have a width that extends beyond the elbow of the patient when positioned on the patient's arm. The exemplary blood pressure cuffs of the present disclosure are configured to overcome this deficiency.

Moreover, while AAMI standards would require increasing the width of known cuffs in conjunction with lengthening the cuff to fit such circumferences, the standard increase in width would result in a blood pressure cuff wider than the distance between the armpit and elbow of most obese patients. The exemplary blood pressure cuffs of the present disclosure, on the other hand, are dimensioned to fit between the armpit and elbow of such patients. In addition, the exemplary bladders described herein are configured such that at least three inches of the width of the bladder and/or at least ⅗ of the width of the bladder contacting the patient's arm may remain in contact with the arm while the blood pressure cuff occludes the patient's brachial artery. In exemplary embodiments, such a width or "contact zone" may be at least three inches wide and/or at least ⅗ of the width of the bladder, and may be configured to maintain contact with the arm of the patient while occluding the brachial artery. Such contact enables an appropriate length of the artery to be occluded during measurement, thereby resulting in an accurate blood pressure reading.

As shown in FIG. 19, this degree of contact, however, would not be possible with standard single-bladder cuffs having similar dimensions due to limited bladder height H5 when inflated. Instead, a bladder 114 of such conventional cuffs would form a substantially circular cross-section about a limb 80 (such as an arm) of a patient 82 at the inflation pressures required for occlusion of the brachial artery 88 in obese patients (typically approximately 160 mm Hg) Such a cross-sectional shape would minimize contact with the patient's arm 80 during measurement, thereby resulting in spot-occlusion or inefficient occlusion of the artery 88 and erroneously high pressure readings.

Generally, a contact zone having a width that is at least 50 percent of the maximum deflated width of the blood pressure cuff is required to obtain an accurate blood pressure measurement. However, when conventional blood pressure cuffs, such as the cuff shown in FIG. 19, are used to occlude the brachial artery 88 in an arm 80 of an obese patient, a width W5 of a contact zone created by such cuffs is typically much less than 50 percent of the corresponding maximum deflated cuff width. As a result, although the width W5 of the contact zone of the bladder 114 may maintain contact with the arm 80 of the patient 82 while the brachial artery 88 is occluded, the relatively minimal width W5 of such a contact zone may erroneously augment blood pressure readings.

Figure 10:
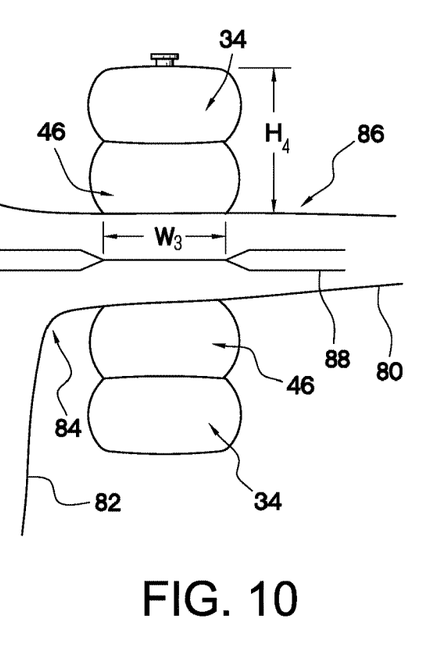
FIG. 10 illustrates an exemplary blood pressure cuff disposed about a limb of a patient.

As shown in FIG. 10, an exemplary blood pressure cuff of the present disclosure may be wrapped around, secured to, and/or otherwise worn on the arm and/or other limb 80 of a patient 82. Although the exemplary blood pressure cuff configuration of FIGS. 3-6 is illustrated in FIG. 10 for ease of description, any of the exemplary blood pressure cuffs described herein may be utilized in accordance with the methods described below.

Once properly positioned between an armpit 84 and an elbow 86 of the patient 82, the blood pressure cuff may be inflated to the inflated height H4, and the height H4 may be greater than the height H5 described above with respect to the conventional blood pressure cuff of FIG. 19. Inflating the blood pressure cuff shown in FIG. 10 may cause an artery 88, such as the brachial artery, of the patient 82 to become occluded, thereby blocking a flow of blood from the heart through the artery 88. The inflation of the blood pressure cuff may be accomplished by connecting, for example, a pump, bulb, and/or other like inflation device to the port 22. Such devices may force a fluid, such as compressed air, into the first bladder 34. Such a fluid may then pass to the second bladder 46 via the one or more passages 54 described above. In exemplary embodiments, the blood pressure cuff may be inflated to at least 160 mm Hg, above which the brachial artery 88 may be occluded.

In an inflated state, the second bladder 46 may maintain contact with the arm and/or other limb 80 of the patient 82 while the brachial artery 88 is occluded. In exemplary embodiments, a width W3 (i.e., the contact zone) of at least three inches of the second bladder 46 may maintain contact with the arm 80 of the patient 82 while the brachial artery 88 is occluded. The width W3 of the contact zone shown in FIG. 10 may be larger than, for example, the width W5 of the contact zone shown in FIG. 19. In addition, the height H4 may be approximately twice the height H5. As a result of this exemplary configuration, the first and second bladders 34, 46 shown in FIG. 10 may be inflatable to a combined height H4 that is greater than twice the maximum (deflated) width W1 described above divided by Pi. This relationship between the combined inflated height H4 of the bladders 34, 46 and the maximum width W1 may result in a blood pressure cuff having an increased contact zone width W3 for a given overall cuff width. For example, such a relationship may result in a contact zone of sufficient width W3 to efficiently occlude the brachial artery 88 in patients 82 having arms 80 of larger than normal circumference. Such an increased contact zone width W3 may result from the relatively uninhibited expansion of the bladders 34, 46 in the direction of the arm 80.

The blood pressure of the patient 82 may then be measured utilizing, for example, a sphygmomanometer and a stethoscope, and/or other like devices. For example, the blood pressure of the patient 82 may be measured in conjunction with slowly releasing fluid from the blood pressure cuff. The pressure at which blood flow can first be heard within the artery 88 may be measured (systolic blood pressure), and as the fluid continues to exit the cuff, the pressure may again be measured when no sound within the artery 88 can be heard (diastolic blood pressure).

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A blood pressure cuff, comprising:
   a first bladder comprising a top, and a bottom separate from and opposite the top, the top being sealed to the bottom, the first bladder having a first width, and a first length transverse to the first width;
   a second bladder fluidly connected to the first bladder via a passage, the second bladder having a second width substantially equal to the first width, and a second length substantially equal to the first length;
   a port fluidly connected to the first bladder, the port comprising a cylindrical central cavity, and a ridge disposed at a distal end of the port, the ridge extending radially away from the central cavity and being configured to connect with a fitting separate from the blood pressure cuff, wherein inflation of the first bladder via the port causes at least partial inflation of the second bladder via the passage; and
   a tail formed by the top of the first bladder and the bottom of the first bladder, the tail including a slot configured to overlay the port and accept passage of the ridge therethrough when the blood pressure cuff is worn by a patient.

2. The blood pressure cuff of claim 1, wherein the passage comprises a first passage disposed opposite the port, the blood pressure cuff further comprising a second passage disposed opposite the port, the second passage fluidly connecting the first bladder with the second bladder, the first passage being spaced from the second passage along a longitudinal axis of the blood pressure cuff.

3. The blood pressure cuff of claim 1, wherein the first bladder is inflatable to a first height, and the second bladder is inflatable to a second height substantially equal to the first height.

4. The blood pressure cuff of claim 1, wherein when the first and second bladders are in an inflated state, a bottom of the second bladder includes a contact zone at least 3 inches wide.

5. The blood pressure cuff of claim 1, wherein the first bladder includes a first orifice disposed opposite the port, and a top of the second bladder includes a second orifice, the first and second orifices forming respective portions of the passage and permitting fluid to pass between the first and second bladders.

6. The blood pressure cuff of claim 5, wherein the bottom of the first bladder is sealed to the top of the second bladder about a perimeter of the first orifice.

7. The blood pressure cuff of claim 1, wherein the first and second bladders are inflatable to a combined height that is greater than twice the width of the first bladder divided by Pi.

8. The blood pressure cuff of claim 1, wherein the second bladder is removably attachable to the first bladder.

9. The blood pressure cuff of claim 8, wherein: the first bladder includes an additional fitting,
the second bladder includes an additional port defining at least part of the passage, and
the additional port mates with the additional fitting to form a removable connection between the first and second bladders.

10. The blood pressure cuff of claim 9, wherein the additional fitting includes a gasket forming a fluid-tight seal at the passage when the second bladder is disconnected from the first bladder.

11. The blood pressure cuff of claim 1, wherein the first bladder is sealed to the second bladder.

12. A blood pressure cuff, comprising:
a first bladder including a top sealed to a bottom opposite the top, the first bladder having a width, and a length equal to approximately three times the width;
a second bladder fluidly connected to the first bladder, the second bladder including a top sealed to the bottom of the first bladder, and a bottom sealed to the top of the second bladder, the second bladder having a length and a width approximately equal to the respective length and width of the first bladder;
a port sealed to the top of the first bladder, the port fluidly connected to the first bladder, the port comprising a cylindrical central cavity, and a ridge disposed opposite the top of the first bladder, the ridge extending radially away from the central cavity and being configured to connect with a fitting for inflation of the first bladder and the second bladder; and
a tail formed by the top of the first bladder and the bottom of the first bladder, the tail including a slot configured to overlay the port and accept passage of the ridge therethrough.

13. The blood pressure cuff of claim 12, wherein the bottom of the first bladder includes a first orifice and the top of the second bladder includes a second orifice, a perimeter of the first orifice being sealed to a perimeter of the second orifice to permit the passage of fluid between the first and second bladders.

14. The blood pressure cuff of claim 13, wherein the first and second orifices comprise corresponding elongated orifices disposed along a central longitudinal axis of the blood pressure cuff.

15. The blood pressure cuff of claim 12, wherein;
the blood pressure cuff includes a first passage disposed opposite the port and fluidly connecting the first bladder with the second bladder, and a second passage disposed opposite the port and fluidly connecting the first bladder with the second bladder, the first passage being spaced from the second passage along a longitudinal axis of the blood pressure cuff.

16. The blood pressure cuff of claim 12, wherein a fluid pressure within the first bladder is substantially equal to a fluid pressure within the second bladder while occluding a brachial artery of a patient.

17. The blood pressure cuff of claim 12, wherein the length of the first bladder is greater than approximately 11 inches and the width of the first bladder is less than approximately 7 inches.

* * * * *